United States Patent [19]
Kühne

[11] Patent Number: 6,086,922
[45] Date of Patent: Jul. 11, 2000

[54] USE OF A CHEMICALLY-STABILIZED CHLORITE MATRIX FOR THE PARENTERAL TREATMENT OF HIV INFECTIONS

[75] Inventor: Friedrich W. Kühne, Heidelberg, Germany

[73] Assignee: Oxo Chemie AG, Friborg/Schweiz, Switzerland

[21] Appl. No.: 08/034,849

[22] Filed: Mar. 19, 1993

[30] Foreign Application Priority Data

Mar. 19, 1992 [DE] Germany ............... 42 08 828

[51] Int. Cl.[7] .................... A61K 33/22; A61K 33/14
[52] U.S. Cl. ............................ 424/660; 424/665
[58] Field of Search ................... 424/665, 660

[56] References Cited

U.S. PATENT DOCUMENTS

| | | | |
|---|---|---|---|
| 4,296,103 | 10/1981 | Laso | 424/130 |
| 4,507,285 | 3/1985 | Kühne | 424/130 |
| 4,725,437 | 2/1988 | Kuhne | 424/130 |
| 5,019,402 | 5/1991 | Kross et al. | 424/665 |

FOREIGN PATENT DOCUMENTS

| | | |
|---|---|---|
| 0 200 155 | 11/1986 | European Pat. Off. . |
| 0 200 156 | 11/1986 | European Pat. Off. . |
| 0 200 157 | 11/1986 | European Pat. Off. . |
| 0481732 | 3/1938 | United Kingdom . |
| 8 903 179 | 4/1989 | WIPO . |
| 8 910 747 | 11/1989 | WIPO . |
| 9 001 315 | 2/1990 | WIPO . |

OTHER PUBLICATIONS

Mar. Index 10th Ed # 4865 1983.

*Primary Examiner*—Marianne M. Cintins
*Attorney, Agent, or Firm*—Foley & Lardner

[57] ABSTRACT

The present invention is concerned with the use of a chemically-stabilized chlorite matrix for the parenteral treatment of HIV infections. The chlorite matrix is an isotonic solution containing 5 to 100 mMol $ClO_2^-$ per liter of solution.

13 Claims, 5 Drawing Sheets

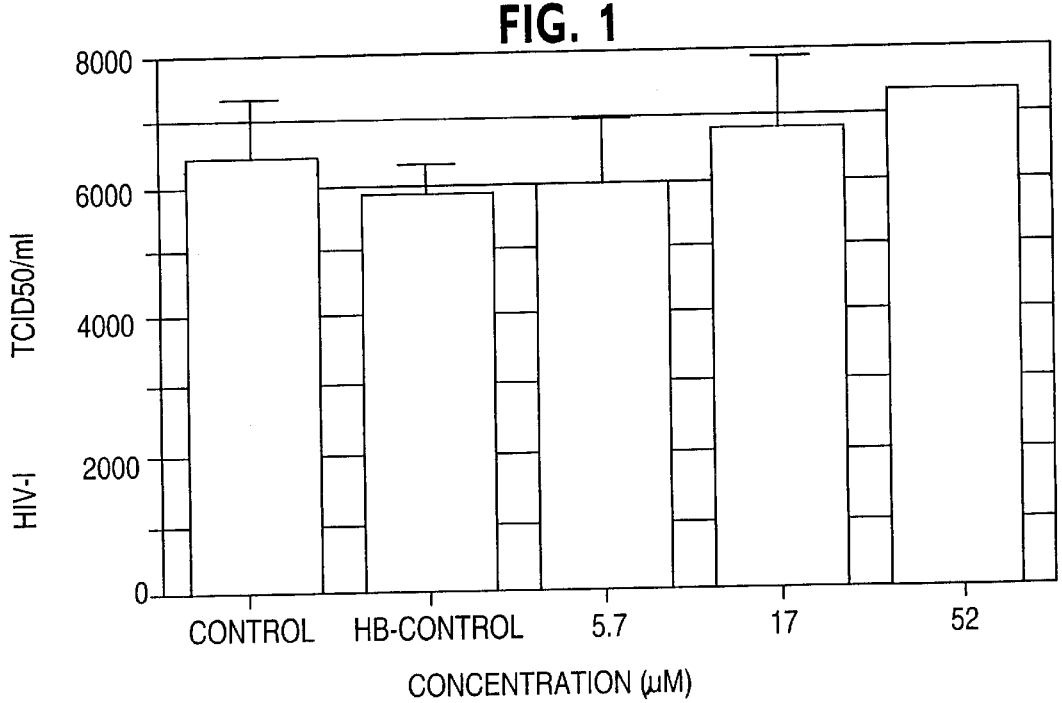
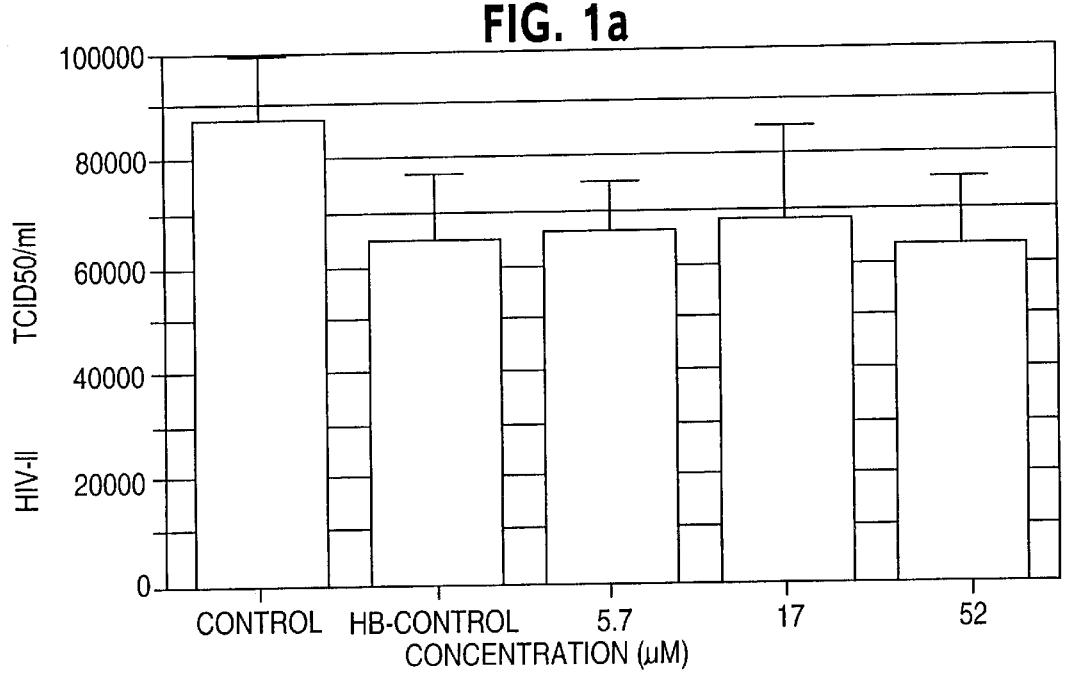

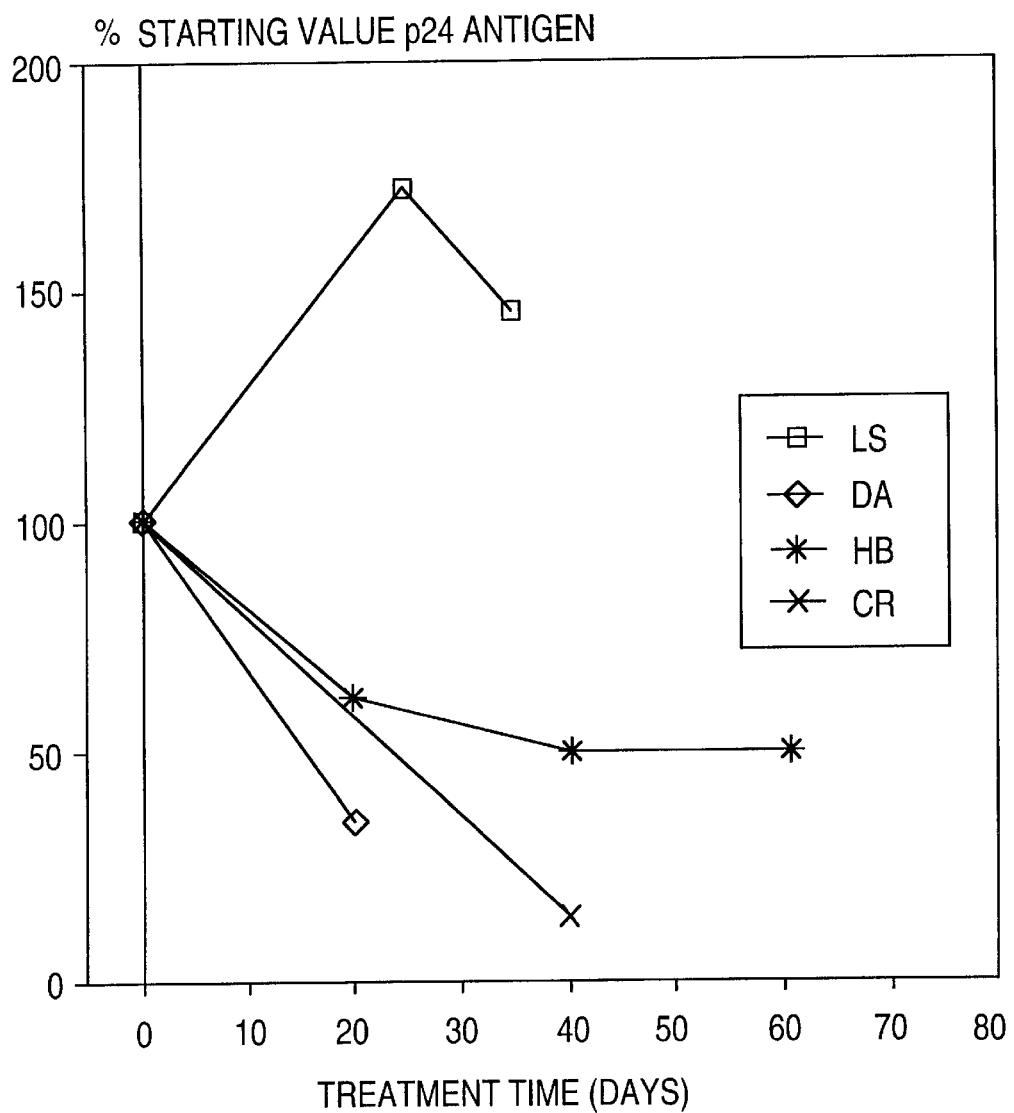

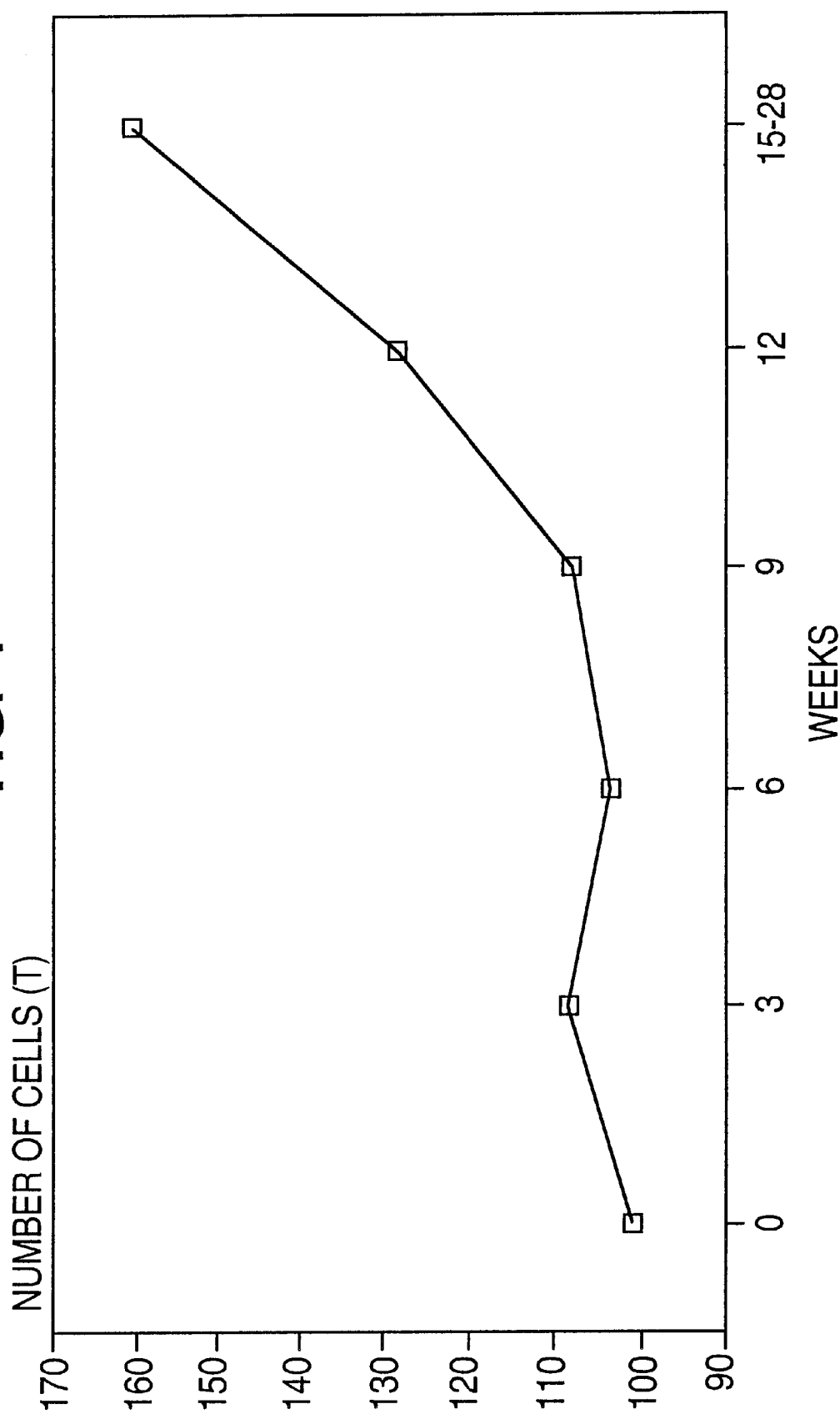

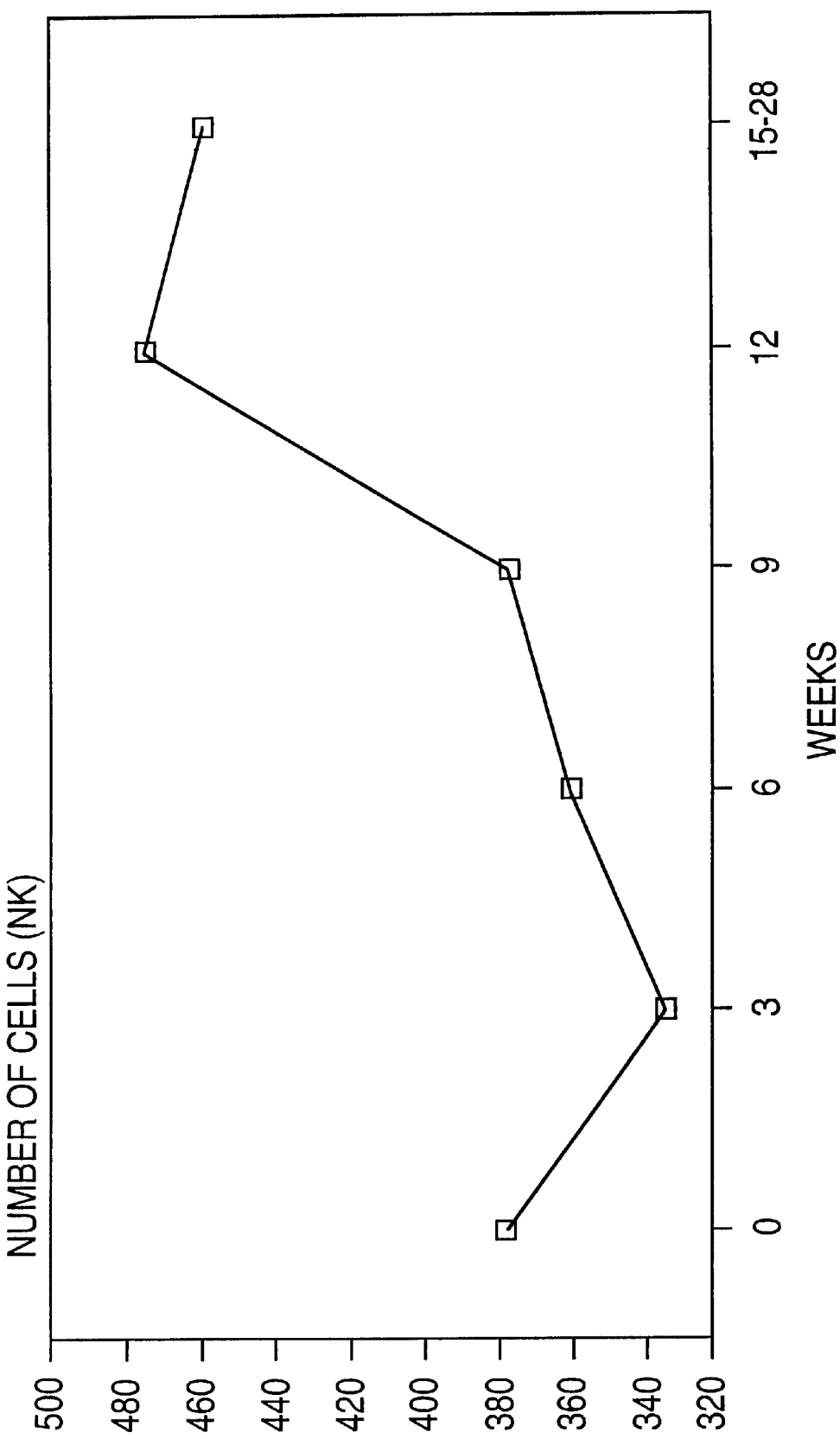

USE OF A CHEMICALLY-STABILIZED CHLORITE MATRIX FOR THE PARENTERAL TREATMENT OF HIV INFECTIONS

BACKGROUND OF THE INVENTION

1. Field of the Invention

The present invention is concerned with the novel use of a chemically-stabilized chlorite matrix for the parenteral treatment of HIV infections.

2. Description of Related Art

HIV infections, amongst which the various subsidiary forms of the HIV virus are to be understood, are ever increasing. Despite intensive endeavors to control HIV infections, it has hitherto not been possible to find an absolutely effective counteragent. Previously known agents, for example AZT or DDI, act especially on the cells infected with the virus, which are thereby killed off so that the infection does not proceed further. But these known agents have no effect on the viruses liberated into the blood circulation by the breakup of such cells, which bring about spreading and infection of other cells.

Sarin et al., New England Journal of Medicine, 313, 1416/1985, discloses a treatment of cell cultures of HTLV III—(HIV) viruses in vitro with a 200 fold diluted solution of 0.23% sodium chlorite and 1.26% lactic acid. The treatment of Sarin et al. led to an inactivation of the viruses.

U.S. Pat. No. 5,019,402 discloses a solution containing chlorine dioxide or a chlorine dioxide-liberating mixture of a chlorite, a weakly acidic buffer and a heat-activated saccharide which can be used for the sterilization of stored blood components with the exception of those which contain red blood corpuscles, i.e., of leukocytes, blood platelets, coagulation factors and globulins. In whole blood, a corresponding disinfecting action does not occur, presumably because the red blood corpuscles are attacked more quickly by the chlorine dioxide than the investigated microorganisms. Therefore, this agent also is not suitable for a parenteral administration.

DE-OS 32 13 389, U.S. Pat. No. 4,507,285 and U.S. Pat. No. 4,296,103, describe chemically-stabilized chlorite matrices which are suitable for an external or oral therapeutic use. Besides various bacterial infections, the external treatment of virus infections, such as herpes simplex and herpes zoster, is deemed possible in this manner but an intravenous administration for the treatment of HIV infections is not possible.

EP 0 200 155 further describes solutions of a chemically-stabilized chlorite matrix for intravenous and perioperative administration. The agent has proved to be effective in the treatment of *Candida albicans* infections. From EP 0 200 157, it is known to use such stabilized chlorite matrices for intravenous and/or local administration in cases of infectious conditions brought about by parasites, fungi, bacteria, viruses and/or mycoplasts. The action is explained by a phagocyte stimulation which is achieved by a single effective administration of the chlorite complex shortly after the infection. Combating virus infections is not described in this publication and, because of the principle of action, does not appear to be possible.

SUMMARY OF THE INVENTION

It is an object of the present invention to provide an agent which inactivates HIV viruses in the blood without having a damaging influence on the blood and on the body of the patient.

In accordance with the present invention, there is provided a method of using a chemically-stabilized chlorite matrix for the parenteral treatment of HIV infections consisting of an isotonic solution containing 5 to 100 mMol, and preferably 50 to 80 mMol of $ClO_2^-$ per liter of solution.

The solution can be used as an injection solution or, after dilution, as an infusion solution.

In accordance with the present invention, there is also provided a method for parenteral treatment of HIV infections comprising administering an inhibition effective amount of a chlorite matrix solution comprising an isotonic solution comprising 5 to 100 mMol of $ClO_{2-}$ per liter of solution. The method of the present invention causes an inhibition of the infection of undamaged cells as well as a stimulation of T-cells and Natural Killer (NK) cells.

Further objects, features and advantages of the present invention will become apparent from the detailed description of preferred embodiments that follow.

BRIEF DESCRIPTION OF THE DRAWINGS

FIGS. 1 and 1a illustrate the relationship between the concentration of chlorite matrix solution and the infectivity of cell-bound HIV-I or HIV-II.

FIG. 3 illustrates the results of Example 3 wherein 4 HIV-I infected patients were treated with chlorite matrix solutions over an extended period of time.

FIG. 4 illustrates the results of Example 4 showing the relationship between the number of T-cells and the period of treatment with the chlorite matrix solutions of the invention.

FIG. 5 illustrates the results of Example 4 showing the relationship between the number of NK cells and the period of treatment with a chlorite matrix solution of the present invention.

DETAILED DESCRIPTION OF THE PREFERRED EMBODIMENTS

Figure 2:
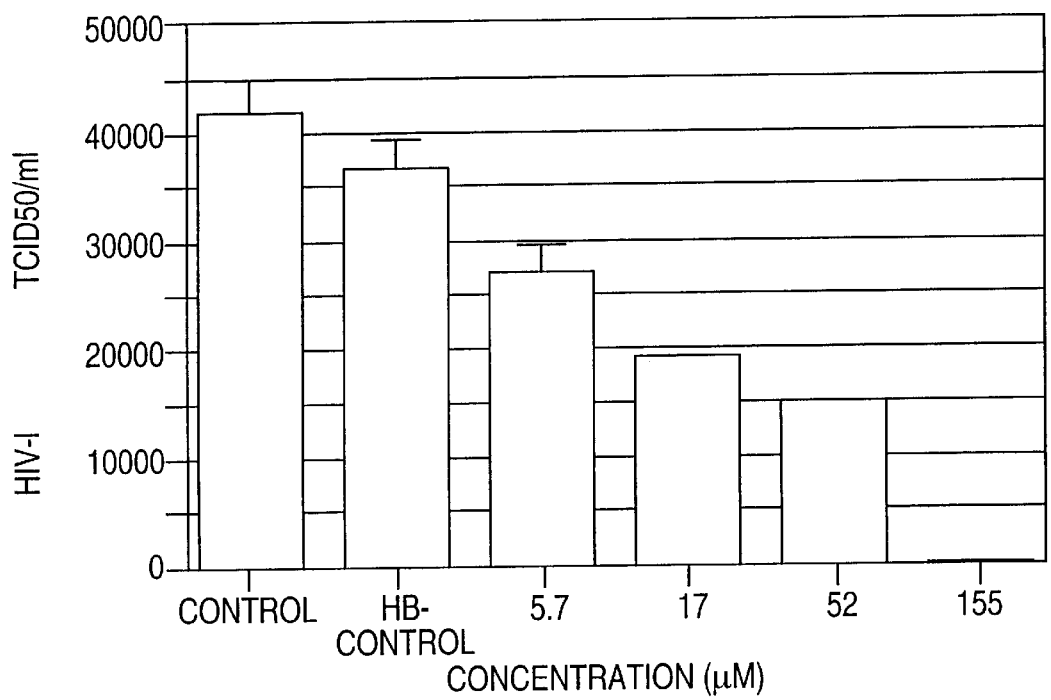
FIGS. 2 and 2a illustrate the relationship between the concentrations of chlorite matrix solution and the infectivity of non cell-bound HIV-I or HIV-II.

Solutions of sodium and potassium chlorite are known to be disproportionate in acidic solution with the formation of chlorine dioxide and chloride. The chlorites and also chlorine dioxide formed are known to be effective microbicides for the sterilization of surfaces and solutions. However, the use of chlorite solutions for parenteral administration typically was not thought to be possible because of their extraordinary toxicity.

It is therefore quite unexpected that, with an intravenous administration of an appropriate chlorite matrix in the appropriate concentration, HIV viruses can be directly combatted in the blood, demonstrated by the rapid and strong decrease of the viruses detectable in the blood. The chlorite matrix solutions of the present invention also do not exhibit adverse effects such as severe cytotoxic damage and the like, typically associated with highly toxic chemicals which are administered intravenously. The chlorite matrix solutions of the present invention further are capable of inactivating the HIV virus to thereby inhibit infection of undamaged cells. The concentration of the HIV virus in serum is typically determined in the known manner by coupling with antibodies against the virus-specific p24 antigen. (S. Mihm et al., (1991) Aids 5, 497–503) The virus-inhibiting action of the chlorite matrix appears to be concentration-dependent. A significant inhibition of a new infection is found in vitro even at concentrations of 5 $\mu$mol/l, whereas a concentration of 150 μmol/l brings about a practically complete inhibition. However, concentrations of more than 100 μmol/l can, over a prolonged period of time, lead to cytotoxic damage. Thus, concentrations of from 10 to 100, preferably of from about 40 to 80 and especially of 50 μmol/l are preferred.

The chlorite matrix solutions of the present invention are dosed in vivo corresponding to the body weight, whereby, because of the continuous breakdown of the active material in the blood, the agent must be administered again at regular intervals. Those skilled in the art are capable of varying the concentrations of virus-inhibiting solutions depending on available in vitro data and body weight. Thus, throughout the specification and claims, the phrase "an inhibition effective amount" will be known by those skilled in the art to mean an amount of solution which, when administered in vivo to subjects of varying weight, will bring about an inhibition of the virus. Typically, an inhibition effective amount of the chlorite matrix solution will vary between about 0.1 ml/kg to about 1.5 ml/kg, preferably, about 0.5 ml/kg of body weight and at a concentration of about 40 to about 80 mMol $ClO_2^-$ per liter, preferably about 60 mMol $ClO_2^-$ per liter, respectively.

The following examples serve to illustrate particularly preferred embodiments of the present invention. Those skilled in the art recognize that various modifications may be made to the foregoing description and the following examples without departing from the spirit and scope of the invention.

EXAMPLE 1

The chlorite matrix, designated as WF10 in the following experiments, was produced in accordance with Example 1 of U.S. Pat. No. 4,507,285 which is hereby incorporated by reference by the oxidation of a chlorite solution with hypochlorite, reaction with perborate or percarbonate and dilution with an isotonic solution of sodium chloride or an appropriate nutrient medium to the concentrations given in the following examples.

In Vitro Experiments

In order to investigate the effectiveness of WF10 on the HIV multiplication in human cell lines, the infectiousness (TCID50), the activity of the reverse transcriptase (RT) and the formation of HIV antigen p24 were investigated.

Human T-lymphoma cells molt-4, clone-8 cells ("molt 4/8 cells") (available from ATCC, Rockville, U.S.A.) permanently infected by HIV-1 were cultured with RPMI-1640 medium (available from Gibco Ltd., GB) which was mixed with 10% fetal calf serum, L-glutamic acid and antibiotics. The human monocyte macrophage cell line U937 (available from ATCC, Rockville, U.S.A.) and primary mononuclear blood cells (PWMC), which were permanently infected with HIV-1, were investigated in the same manner.

For the measurement of the activity of the HIV reverse transcriptase, 1 ml of the culture supernatant was investigated with a standard enzyme investigation system which depended upon the incorporation of radio-actively-labelled nucleotides. This determination gave an indication of the possible effect of the substance on the spread of HIV infection.

The concentration of the HIV nucleus antigen p24 was investigated in the supernatant by Elisa techniques with a commercially-available kit (Abbot Labs, Chicago, U.S.A.) which contained an internal standard. The concentrations given in the following Tables are in ng/ml of culture liquid. In the test, no differentiation was made between p24 antigen and infectious or inactivated HIV viruses.

The infectivity of the HIV (TCID50) was determined by bringing the HIV-containing solution together with the highly-sensitive MT4 cells (American Tissue Collection Rockville, U.S.A.) which are killed off within a short time by infectious HIV-1 (S. G. Norley., 1990) I. Immunol. 145, 1700–1705). The infectivity was shown by the remaining growth of the cell colony. Furthermore, the cytopathic effect can be determined by the rate of incorporation of $^3$H-thymidine since killed-off cells can no longer incorporate thymidine into their DNA. Thus, from the strength of the thymidine incorporation or the radio-activity thereby brought about by the cell DNA separated from the solution, the amount of the surviving cells can be deduced.

Those skilled in the art are well-versed in these techniques, and the methods employed above for measuring infectivity, concentration of the p24 antigen, and the activity of HIV reverse transcriptase are adequate described in the scientific literature.

Multiplication of HIV in the Presence of WF10.

Approximately $2 \times 10^6$ molt 4/8 cells which were permanently infected with HIV-I were incubated on a 24-cup culture plate in 2 ml of culture medium for 24 hours in the presence of different concentrations of WF10, with and without the addition of hemoglobin (see the following Table 1). The same protocol was carried out, only the molt 4/8 cells were infected-with HIV-II. The results are shown in FIGS. 1 and 1a.

TABLE 1

Treatment of HIV-Infected cells with WF10

| No. | Substance | Concentration | Addition |
|-----|-----------|---------------|----------|
| 1   | —         | —             | —        |
| 2   | —         | —             | Hb$^a$   |
| 3   | WF10      | 1.9 μM        | —        |
| 4   | WF10      | 5.7 μM        | —        |
| 5   | WF10      | 17.2 μM       | —        |
| 6   | WF10      | 51.7 μM       | —        |
| 7   | WF10      | 1.9 μM        | Hb       |
| 8   | WF10      | 5.7 μM        | Hb       |
| 9   | WF10      | 17.2 μM       | Hb       |
| 10  | WF10      | 51.7 μM       | Hb       |

$^a$HB = hemoglobin (250 μg/ml)

From FIGS. 1 and 1a of the accompanying drawings, it can be inferred that, for the investigated concentrations of 5.7 to 53 μmol, the TCID50/ml is not significantly different from the control. Consequently, WF10 has little or no marked effect on cell-bound HIV-I or HIV-II.

EXAMPLE 2

Infectivity of Non-bound HIV after Incubation with WF10

Figure 2A:
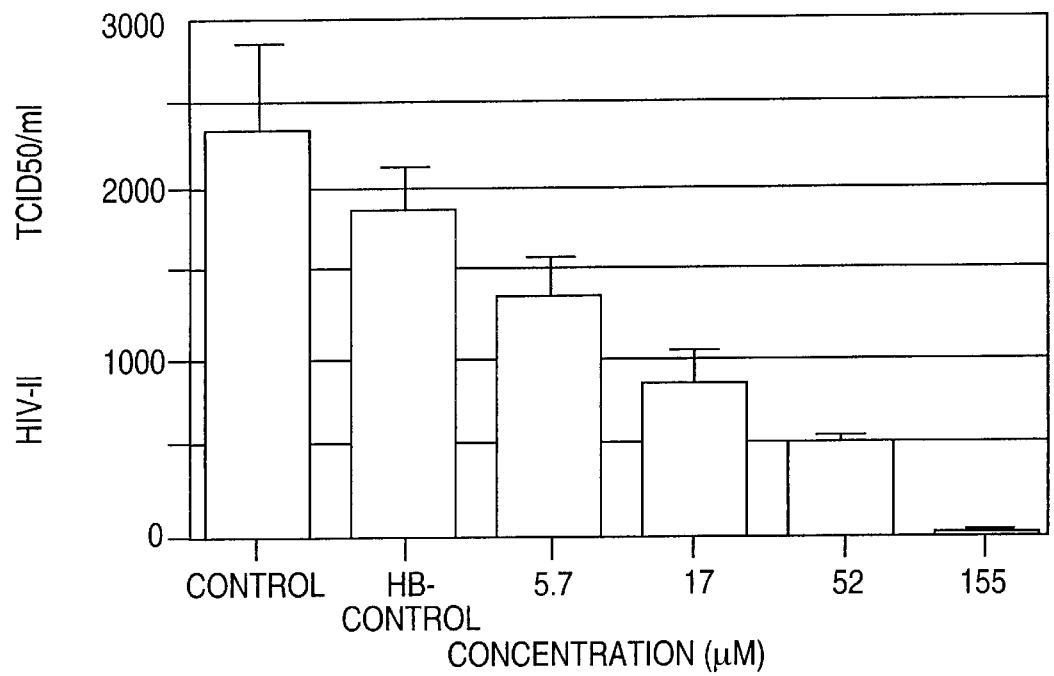

In order to investigate the possible inactivation by WF10 of free HIV particles, the WF10 dilutions and control solutions given in the following Table 2 were incubated with a corresponding HIV parent solution for the given times. The results obtained are shown in FIGS. 2 and 2a of the accompany drawings.

It is shown that WF10 effectively inhibits HIV viruses in the investigated concentration.

TABLE 2

Inactivation of HIV by WF10

| No. | Substance | Concentration | Addition | Time   |
|-----|-----------|---------------|----------|--------|
| 1   | —         | —             | —        | 30 min |
| 2   | —         | —             | Hb$^a$   | —      |
| 3   | WF10      | 155 μM        | —        | —      |

TABLE 2-continued

Inactivation of HIV by WF10

| No. | Substance | Concentration | Addition | Time |
|-----|-----------|---------------|----------|------|
| 4   | WF10      | 155 μM        | Hb       | —    |
| 5   | —         | —             | —        | 1 hr |
| 6   | —         | —             | Hb       | —    |
| 7   | WF10      | 155 μM        | —        | —    |
| 8   | WF10      | 155 μM        | Hb       | —    |
| 9   | —         | —             | —        | 3 hrs|
| 10  | —         | —             | Hb       | —    |
| 11  | WF10      | 155 μM        | —        | —    |
| 12  | WF10      | 155 μM        | Hb       | —    |
| 13  | —         | —             | —        | 6 hrs|
| 14  | —         | —             | Hb       | —    |
| 15  | WF10      | 155 μM        | —        | —    |
| 16  | WF10      | 155 μM        | Hb       | —    |
| 17  | —         | —             | —        | —    |
| 18  | —         | —             | Hb       | 18 hrs |
| 19  | WF10      | 155 μM        | —        | —    |
| 20  | WF10      | 155 μM        | Hb       | —    | a Hb = hemoglobin (250 μg/ml)

EXAMPLE 3

New Infection of Cells with HIV in the Presence of WF10

In a further experiment, the degree of spreading of the virus in cell cultures after infection with HIV was determined.

Cultures of molt 4/8 were infected with HIV-I parent solution in various dilutions. In each case, the culture medium was exchanged after two days and the infectivity determined in the supernatant with MT4 cells as described above in Example 1. Insofar as the solution contained an active material (WF10, AZT or DDI combinations thereof), these were, in the case of the exchange, in each case again added to the culture medium in the appropriate concentration.

In Vivo Experiments

The agents used according to the present invention were tested on a small group of patients with acute HIV infection. For this purpose, about 0.5 ml/kg of body weight of WF10 with a concentration of 60 mMol/l $ClO_{2-}$ was injected into the patients, in each case on five successive days of a week, followed by a pause of two weeks. The p24 antigen concentration was then determined and the treatment further continued one to three times in the same cycle. The results obtained are reproduced in the following Table 3.

The influence on the serum level of p24 antigen in the case of 4 HIV-I-infected patients who had been correspondingly treated with WF10 is given in the following Table 3, as well as FIG. 3 of the accompanying drawings, referenced to the value before the treatment, which is taken as being 100%. These patients are labelled LS, DA, HB and CR wherein LS is the only patient which exhibited an increase in the p24 antigen. It can be seen that, in all other cases, a very rapid, strong decrease is noticed which also continues over the comparatively long period of treatment. The patient LS is an exception: originally, this patient had a very low titre of p24 AG, the titre first increasing and only after the 30th day again falling significantly. Since the titre of the p24 antigen is a measure for the concentration of the viruses in the serum, it is to be assumed from this finding that WF10 directly attacks and inactivates the unbound viruses and thus is able to inhibit the new infection of not yet damaged cells.

TABLE 3 p 24 AG con. (pg/ml and % of starting value) for treatment with WF10

| Patient | CR | | DA | | LS | | HB | |
|---------|-----|------|-----|------|-----|-------|------|------|
| Date    | I   | %    |     | %    |     | %     |      | %    |
| 0       | 666 | 100.0| 483 | 100.0| 173 | 100.0 | 5363 | 100.0|
| 19      | —   | —    | 169 | 35.0 | —   | —     | —    | —    |
| 21      | —   | —    | —   | —    | —   | —     | 3353 | 62.5 |
| 28      | —   | —    | —   | —    | 300 | 173.4 | —    | —    |
| 35      | —   | —    | —   | —    | 253 | 146.2 | —    | —    |
| 39      | 95  | 14.3 | —   | —    | —   | —     | —    | —    |
| 42      | —   | —    | —   | —    | —   | —     | 2713 | 50.6 |
| 63      | —   | —    | —   | —    | —   | —     | 2603 | 48.5 |

EXAMPLE 4

The concentration of the T-cells and NK cells, which is important for the immune defense system of the body, was determined during the treatment of the 4 patients above in Example 3 with WF10. It was found that the number of cells important for the immune defense begins to increase after a period of treatment of nine weeks. Hence, a long-term immunization can be stimulated by treatment with WF10. The short-term sinking of the p24 antigen concentration observed in the case of administration of WF10 cannot, however, be explained on the basis of this mechanism, which is a further indication that there exists a direct exchange action of WF10 with the free, unbound viruses. The experimental results obtained are given in FIGS. 4 and 5 of the accompanying drawings. These results show that T-cell and NK cells were stimulated after an extended treatment with the chlorite matrix solution of the present invention.

What is claimed is:

1. A method of parenterally treating HIV infections, comprising administering to a subject in need of such treatment an inhibition-effective amount of a chemically-stabilized chlorite matrix comprising an isotonic solution containing about 5 to about 100 mMol $ClO_{2-}$ per liter of isotonic solution.

2. A method according to claim 1, wherein the solution contains about 50 to about 80 mMol $ClO_{2-}$ per liter of isotonic solution.

3. A method according to claim 1, wherein the chemically-stabilized chlorite matrix is administered as an injection solution or an infusion solution after dilution with water.

4. A method according to claim 2, wherein the chemically-stabilized chlorite matrix is administered as an injection solution or an infusion solution after dilution with water.

5. A method according to claim 1, wherein said chlorite matrix is produced by oxidation of a chlorite solution with hypochlorite and reaction with perborate.

6. A method according to claim 2, wherein said chlorite matrix is produced by oxidation of a chlorite solution with hypochlorite and reaction with percarbonate.

7. A method according to claim 1, wherein the solution contains about 50 mMol $ClO_{2-}$ per liter of isotonic solution.

8. A method according to claim 1, wherein said chlorite matrix is administered in an amount of about 0.1 to about 1.5 ml/kg of body weight with a concentration of about 40 to about 80 mMol $ClO_{2-}$ per liter of isotonic solution.

9. A method according to claim 8, wherein said chlorite matrix is administered in an amount of about 0.5 ml/kg of body weight with a concentration of about 60 mMol $ClO_2^-$ per liter of isotonic solution.

10. A method according to claim 1, wherein the unbound HIV virus present in the subject is inactivated by the treatment thereby inhibiting infection of undamaged cells.

11. A method according to claim 1, wherein the concentration of T-cells and NK cells are increased after administration of said chlorite matrix.

12. A method according to claim 5, wherein after reaction with perborate, the solution is diluted with an isotonic solution of sodium chloride.

13. A method according to claim 6, wherein after reaction with percarbonate, the solution is diluted with an isotonic solution of sodium chloride.

\* \* \* \* \*